(12) United States Patent
Jiang et al.

(10) Patent No.: US 11,325,301 B2
(45) Date of Patent: May 10, 2022

(54) 3D PRINTING EQUIPMENT UTILIZING BIOLOGICAL MATERIAL, AND METHOD

(71) Applicants: Qing Jiang, Nanjing (CN); Liya Zhu, Nanjing (CN); Lan Li, Nanjing (CN); Zongan Li, Nanjing (CN); Kelou Li, Nanjing (CN); Jianfei Yang, Nanjing (CN)

(72) Inventors: Qing Jiang, Nanjing (CN); Liya Zhu, Nanjing (CN); Lan Li, Nanjing (CN); Zongan Li, Nanjing (CN); Kelou Li, Nanjing (CN); Jianfei Yang, Nanjing (CN)

(73) Assignees: Qing Jiang, Nanjing (CN); Liya Zhu, Nanjing (CN); Lan Li, Nanjing (CN); Zongan Li, Nanjing (CN); Kelou Li, Nanjing (CN); Jianfei Yang, Nanjing (CN)

( * ) Notice: Subject to any disclaimer, the term of this patent is extended or adjusted under 35 U.S.C. 154(b) by 376 days.

(21) Appl. No.: 16/094,842

(22) PCT Filed: Feb. 27, 2017

(86) PCT No.: PCT/CN2017/075018
§ 371 (c)(1),
(2) Date: Oct. 18, 2018

(87) PCT Pub. No.: WO2017/181773
PCT Pub. Date: Oct. 26, 2017

(65) Prior Publication Data
US 2019/0134902 A1    May 9, 2019

(30) Foreign Application Priority Data

Apr. 20, 2016    (CN) .......................... 201610247342.2

(51) Int. Cl.
*B29C 67/00* (2017.01)
*B29C 64/209* (2017.01)
(Continued)

(52) U.S. Cl.
CPC ............ *B29C 64/209* (2017.08); *A61L 27/14* (2013.01); *A61L 27/16* (2013.01); *A61L 27/38* (2013.01);
(Continued)

(58) Field of Classification Search
CPC ....... A61L 27/14; A61L 27/38; B29C 64/106; B29C 64/209; B29C 64/264;
(Continued)

(56) References Cited

U.S. PATENT DOCUMENTS

| 2016/0059481 A1* | 3/2016 | Starodubtsev | B29C 64/112 264/494 |
| 2016/0060449 A1* | 3/2016 | Shulga | B29C 64/118 252/62.54 |
| 2017/0095976 A1* | 4/2017 | Pedersen | B29C 64/118 |

FOREIGN PATENT DOCUMENTS

| CN | 103171151 A | 6/2013 |
| CN | 204773637 U | 11/2015 |

(Continued)

OTHER PUBLICATIONS

PCT/CN2017/075018 International Search Report and International Written Opinion dated May 24, 2017.

*Primary Examiner* — Ryan M Ochylski
(74) *Attorney, Agent, or Firm* — Ling Wu; Stephen Yang; Ling and Yang Intellectual Property

(57) ABSTRACT

3D bioprinting apparatus, and a three-dimensional bioprinting method utilizing the apparatus. The 3D bioprinting apparatus comprises a printer frame (14). A 3D bioprinting
(Continued)

pen device (4) is arranged on the printer frame (14) and includes a detachable printing pen (1).

19 Claims, 6 Drawing Sheets

(51) Int. Cl.
| | |
|---|---|
| *B33Y 10/00* | (2015.01) |
| *B33Y 30/00* | (2015.01) |
| *B29C 64/106* | (2017.01) |
| *B29C 64/264* | (2017.01) |
| *B33Y 50/02* | (2015.01) |
| *A61L 27/14* | (2006.01) |
| *A61L 27/38* | (2006.01) |
| *B33Y 70/00* | (2020.01) |
| *B29C 64/393* | (2017.01) |
| *A61L 27/16* | (2006.01) |
| *B33Y 80/00* | (2015.01) |
| *B29L 31/00* | (2006.01) |
| *B29K 105/00* | (2006.01) |

(52) U.S. Cl.
CPC .......... *B29C 64/106* (2017.08); *B29C 64/264* (2017.08); *B29C 64/393* (2017.08); *B33Y 10/00* (2014.12); *B33Y 30/00* (2014.12); *B33Y 50/02* (2014.12); *B33Y 70/00* (2014.12); *B29K 2105/0035* (2013.01); *B29L 2031/753* (2013.01); *B33Y 80/00* (2014.12)

(58) Field of Classification Search
CPC ....... B29C 64/393; B33Y 10/00; B33Y 30/00; B33Y 50/00; B33Y 50/02; B33Y 70/00
See application file for complete search history.

(56) References Cited

FOREIGN PATENT DOCUMENTS

| | | |
|---|---|---|
| CN | 205097557 U | 3/2016 |
| CN | 10571510 A | 7/2016 |
| CN | 205522545 U | 8/2016 |

\* cited by examiner

3D PRINTING EQUIPMENT UTILIZING BIOLOGICAL MATERIAL, AND METHOD

CROSS-REFERENCE TO RELATED APPLICATIONS

This application is a 371 U.S. National Phase of PCT International Application No. PCT/CN2017/075018 filed on Feb. 27, 2017, which claims priority to Chinese Patent Application No. 201610247342.2 filed on Apr. 20, 2016, both of which contents are incorporated by reference herein in their entireties.

TECHNICAL FIELD

Embodiments of the present invention substantially pertain to, but are not limited to, the technical field of bioprinting in tissue engineering.

BACKGROUND

Tissue engineering is to prepare bioactive artificial substitutes with principles and methods of engineering and life science, for the purpose of maintaining, recovering or improving part or all of the functions of human tissues or organs. Tissue engineering is used for a broad range of applications, including bone and cartilage tissue engineering, skin tissue engineering, heart, liver, kidney or other internal organs or tissues.

3D bioprinting is to print biomaterials (including natural biomaterials and synthetic biomaterials) or cell suspensions in controlled manner with the utilization of the basic principle and method of 3D printing slicing-additive molding, forming desired bioactive implants, 3D cell structures or artificial tissues or organs etc. As an emerging technology crossing both life science and modern manufacturing science, 3D bioprinting is used to facilitating the construction of various 3D bionic structures required in tissue engineering.

Currently, 3D bioprinting technologies can be divided into two major categories: inkjet molding technology and extrusion molding technology. The pneumatic piston extrusion nozzle pushes the biomaterial in the piston extrusion nozzle by continuous pneumatic power provided by the compressed gas, to continuously extrude and mold the biomaterial from the micro-nozzle. Pneumatic extrusion molding has several advantages, such as a wide range of molding materials, high flexibility, and convenience in controlling.

SUMMARY

The following is a summary of the subject matter described in detailed description herein. This summary is not intended to limit the scope of the claims.

The inventors of the present application have found that the existing 3D bioprinting apparatus adopts a fixed molding platform and the nozzle can only work in a limited molding space, thus having the following disadvantages:

1). Existing 3D bioprinting apparatus must finish the printing of 3D biological structures such as implants, tissue engineering scaffolds, tissues or organs in vitro, and cannot print and repair the required tissues or organs in real time within animals or human bodies.

2). The nozzle of the existing 3D bioprinting apparatus can only move by means of a three-dimensional motion device, and is not suitable for the operation of minimally invasive surgery for various tissues or organs.

Therefore, the embodiments of the present invention provide a 3D bioprinting apparatus, which includes a printer frame, a motion control system, a 3D bioprinting pen device, an air pump and an air pressure controller.

The 3D bioprinting pen device is arranged on the printer frame, and the 3D bioprinting pen device includes a detachable printing pen.

In the above or other embodiments, the 3D bioprinting pen device may further include a pen body housing and a connecting piece, and wherein the printing pen may be disposed inside the pen body housing on which the connecting piece may be sleeved, and the pen body housing may be connected to the printer frame by the connecting piece.

In the above or other embodiments, the 3D bioprinting pen device may further include a nozzle sleeve which may be sleeved outside the pen body housing, a rotatable L-shaped fixing latch with a stop arm may be provided over the top of the nozzle sleeve. The stop arm may be configured to block the printing pen when the stop arm is turned to the position on the top of the printing pen, and the printing pen can be detached when the stop arm keeps away from the top of the printing pen.

In the above or other embodiments, through holes are provided on a side of the pen body housing, and a connecting piece through hole is provided in the connecting piece. A bolt passing through the connecting piece through hole and the through hole of the pen body housing may fix the pen body housing to the connecting piece, thereby adjusting the height of the 3D bioprinting pen device.

In the above or other embodiments, the bottom end of the printing pen may include a print head.

In the above or other embodiments, the print head may be a detachable print head, and optionally may be a rotatably detachable print head.

In the above or other embodiments, the printing pen may be provided with a lighting apparatus.

In the above or other embodiments, the print head may be a detachable conical fixed type print head, and the end of the fixed type print head may be provided with a fixed type UV point light source.

In the above or other embodiments, the print head may be a detachable hand-held print head in the shape of an elongated rod, and a hand-held UV point light source may be sleeved on the middle of the hand-held print head.

In the above or other embodiments, the printing pen may be provided with a lighting apparatus switch, optionally a UV point light source switch.

In the above or other embodiments, the printing pen may be provided with an air pump switch.

In the above or other embodiments, a lighting apparatus wiring channel may be provided in the interior of the printing pen, optionally a UV point light source wiring channel.

In the above-mentioned or other embodiments, the air pump and the air pressure controller may be installed outside the printer frame and connected to the printing pen, so that the print head generates droplets under the action of air pressure.

The embodiments of the present invention employ pneumatic extrusion molding and polymer materials and/or biomaterials can be quickly cured or crosslinked at room temperature by means of light irradiation or chemical crosslinking, thereby the molding space is open, and the printing pen can be detached and operated by hand, which facilitates achieving a real-time, minimally invasive and an in-situ printing of tissues or organs.

The embodiments of the present invention also provide a bioprinting method of the 3D bioprinting apparatus based on the open space, including the following steps:

establishing a three-dimensional solid model to be printed, slicing it into layers, acquiring data information of each layer, and inputting the data information of each layer into a motion control system;

preparing required polymer material and/or biomaterial, and placing the polymer material and/or biomaterial in a printing pen;

controlling the printing pen by a motion control system to eject and print polymer material and/or biomaterial, optionally detaching the printing pen and carrying out a hand-held control operation to eject and print the polymer material and/or biomaterial so that the polymer material and/or biomaterial directly act on and bond to a solid structure to be associated with the three-dimensional solid model; and after one layer is printed, the printing pen being lifted by the height of one layer, and the jet printing step is performed again to repeatedly additively perform the printing layer by layer until the printed three-dimensional solid model is directly printed on the solid structure.

In the above or other embodiments, the 3D bioprinting apparatus may be the 3D bioprinting apparatus in accordance with any of the above or other embodiments of the present invention.

In the above or other embodiments, the polymer material and/or biomaterial may be selected from one or more of the following groups: polymer material and/or biomaterial containing cells, polymer material and/or biomaterial containing photoactive material, and polymer material and/or biomaterial containing non-photoactive material.

In the above-mentioned or other embodiments, when the polymer material and/or biomaterial contains photoactive material, light emitted from point light source may be irradiated onto the polymer material and/or biomaterial ejected from the print head at the same time in the molding process of the polymer material and/or biomaterial for curing the polymer material and/or biomaterial.

In the above-mentioned or other embodiments, when the polymer material and/or biomaterial contains a non-photoactive material, the polymer material and/or biomaterial may be ejected onto the base solution in the molding area by a printing pen during the molding process of the polymer material and/or biomaterial, and the solid structure may be formed by chemical crosslinking.

In the above or other embodiments, the solid structure may be a tissue or organ to be repaired, optionally bone tissue, cartilage, liver, kidney, skin, muscle, or blood vessel to be repaired.

The embodiments of the present invention have the following advantageous effects:

(1) The embodiments of the present invention do not include any fixed printing platform, so physicians can place large-sized body tissues or organs of patients such as arms, legs and joints in the forming space of a 3D bioprinter to realize real-time and direct printing repair of bone, cartilage, muscle, skin and other tissues or organs.

(2) The embodiments of the present invention employ a detachable 3D bioprinting pen device, so that physicians can print and repair damaged tissues or organs in a hand-held manner according to real-time image data during operation, and the operation is simple, flexible and minimally invasive.

(3) The embodiments of the present invention can print a plurality of polymer materials and/or biomaterials, can realize forming process at normal temperature by adopting an optional photo curing or crosslinking forming mode, and have the advantages of high curing speed, high cell survival rate and a wide range of applications.

BRIEF DESCRIPTION OF DRAWINGS

The drawings are illustrations for further understanding of embodiments of the present invention and constitute a part of the description. The embodiments of the present invention are described in more detail below referring to the drawings and detailed description, and the drawings and detailed description are not intended to limit the embodiments of the present invention.

DETAILED DESCRIPTION

Embodiments of the present invention will be described in detail below. It should be understood that the specific embodiments described herein are for the purpose of illustration and explanation only and are not intended to limit the present application. It should be noted that the embodiments in this application and the features in the embodiments can be combined with each other in any way if without conflict.

EMBODIMENTS

Figure 1:
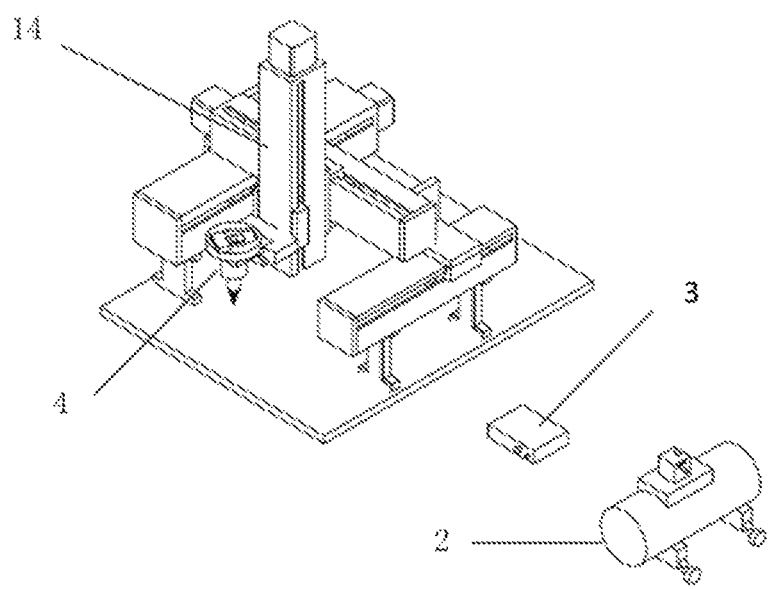
FIG. 1 is a schematic structural diagram of a 3D bioprinting apparatus according to an embodiment of the present invention.
Figure 2:
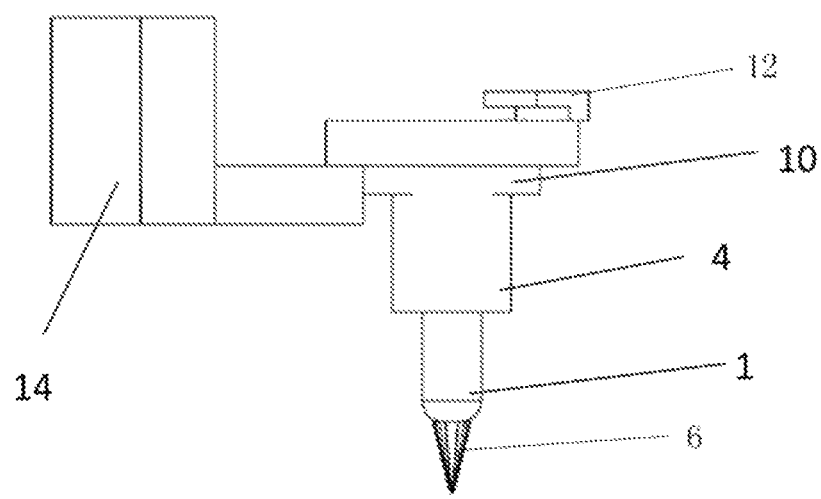
FIG. 2 is a schematic diagram of a 3D bioprinting pen device connected to a printer frame, according to an embodiment of the present invention.
Figure 3:
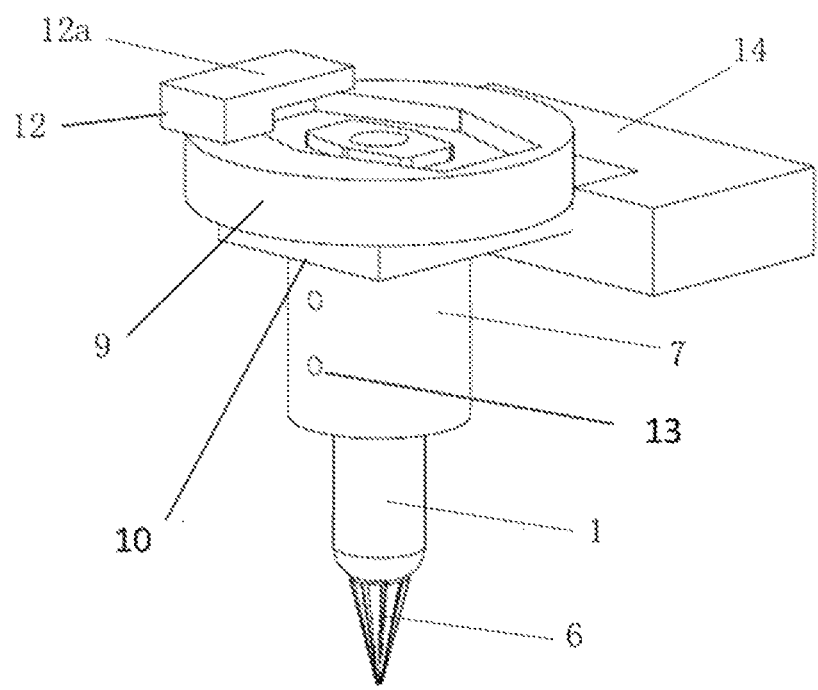
FIG. 3 is a schematic structural diagram of a 3D bioprinting pen device according to an embodiment of the present invention.

As shown in FIGS. 1 to 3, a 3D bioprinting apparatus includes an air pump 2, an air pressure controller 3, a 3D bioprinting pen device 4, and a printer frame 14. The air pump 2, the air pressure controller 3 and the printer frame 14 are sequentially connected, and a detachable 3D bioprinting pen device 4 is provided on the printer frame 14. A detachable printing pen 1 is provided on the 3D bioprinting pen device 4.

Figure 4:
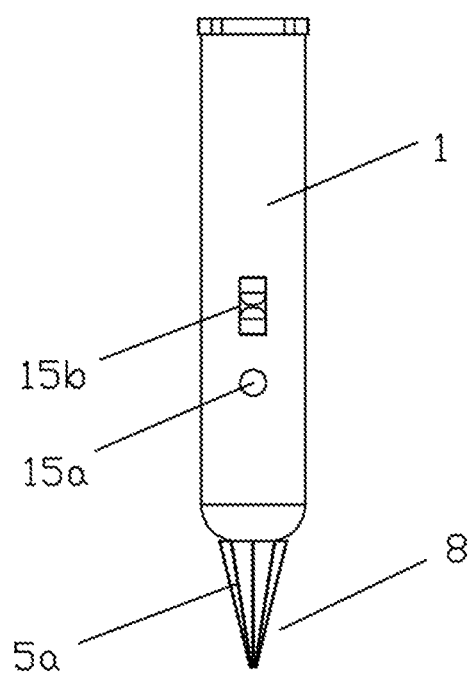
FIG. 4 is a schematic diagram of a fixed type print head according to an embodiment of the present invention.

The air pump 2, the air pressure controller 3 and an air pump hose are sequentially connected, forming a controlling pipeline. The top of the printing pen 1 is connected to the air pump 2 through a duct. In addition, a duct for receiving polymer material and/or biomaterial for 3D printing is provided inside the printing pen 1. As shown in FIG. 4, an air pump switch 15b is provided on the printing pen 1, for controlling the ejection of polymer materials and/or biomaterials.

The 3D bioprinting pen device 4 includes a pen body housing 7 and a detachable printing pen 1 inside the pen body housing 7. The bottom of the printing pen 1 includes a print head 6. A hole is provided in the bottom of the pen body housing 7, through which the print head 6 at the bottom of the printing pen 1 is exposed, so as to facilitate 3D printing. A connecting piece 10 is sleeved on the pen body housing 7, and connected with the printer frame 14 to fix the printing pen 1 on the printer frame 14. A row of through holes 13 are provided on a side of the pen body housing 7, and connecting piece through holes are provided in the connecting piece 10. The pen body housing 7 is fixed to the connecting piece 10 by bolts passing through the connecting piece through holes and the through holes 13 of the pen body housing 7, thereby adjusting the height of the 3D bioprinting pen device 4.

A nozzle sleeve 9 is sleeved on the outer side of the pen body housing 7. The top of the nozzle sleeve 9 is provided with a rotatable L-shaped fixing latch 12 which is provided with a stop arm 12a. The stop arm 12a of the L-shaped fixing latch 12 is used to block the printing pen 1 when it is turned to the position on top of the printing pen 1. The printing pen 1 can be detached and removed when the stop arm 12a of the L-shaped fixing latch 12 keeps away from the top of the printing pen 1.

Turning now to FIG. 4, FIG. 4 is a schematic diagram of a fixed type print head 8. The printing pen 1 includes a conical fixed type print head 8, a UV point light source switch 15a for controlling the light source, and an air pump switch 15b for controlling the air source. The conical fixed type print head 8 is rotatably mounted on the printing pen 1. An end portion of the fixed type print head 8 includes a fixed type UV point light source 5a.

Figure 5:
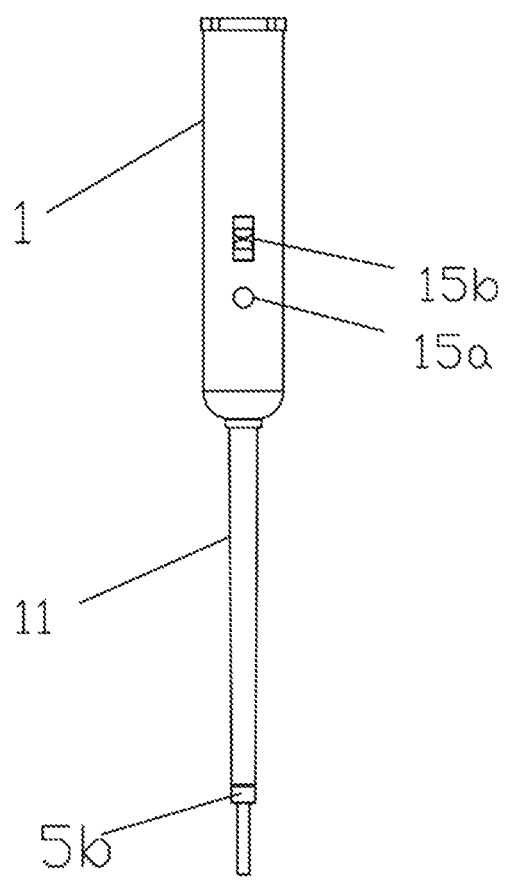
FIG. 5 is a schematic diagram of a detachable hand-held print head according to an embodiment of the present invention.
Figure 6:
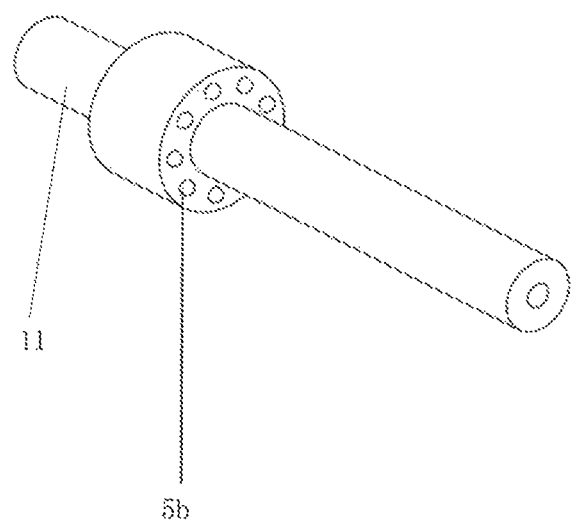
FIG. 6 is an enlarged partial view of a detachable hand-held print head according to an embodiment of the present invention.

Turning now to FIGS. 5 and 6, FIGS. 5 and 6 are schematic and partially enlarged views of a removable hand-held print head 11. The detachable hand-held print head 11 is in the shape of a detachable elongated rod. The hand-held UV point light source 5b is sleeved on the detachable hand-held print head 11 with the light source facing the direction of the head.

The working principle and working process of the embodiments of the 3D bioprinting apparatus are as follows:

(1) designing a three-dimensional solid model through scanning and CAD, and slicing the model by using upper computer processing software;

(2) selecting the experimental materials, preparing the polymer materials and/or biomaterials required for forming process according to a proper proportion, and placing the materials in a printing pen;

(3) sending the data information obtained from the slicing procedure to the motion control system of the lower computer (it is an existing technology that the motion control system is connected with the motor of the frame to control the printer's spatial motion), the motion control system controlling the printing pen to move in X and Y directions according to the received data and control information, the print head 6 ejecting the biomaterial droplets under the action of the air pressure controller 3 so that the biomaterial droplets directly act on and firmly bond to a solid structure to be associated with the three-dimensional solid model, and after the processing of one layer of is finished, the printing pen 1 being lifted by one layer thickness to print the second layer, thus performing the additive forming process layer by layer;

(4) if the applied polymer material and/or biomaterial contains photoactive material, the polymer solution ejected from the print head will quickly set and bond together under the irradiation of the point light source; and if the applied polymer material and/or biomaterial contains non-photoactive material, the polymer solution ejected from the print head 6 and the base solution in the printed area will realize the molding process by the action of chemical crosslinking;

(5) if minimally invasive in-situ printing is required, the 3D bioprinting pen 1 can be detached for direct operation, and the discharge and irradiation of the air pump 2 can be controlled through the air pump switch and the UV point light source switch.

This disclosure is an example of the principles of the embodiments of the present application and is not intended to limit the present application in any form or substance or to specific embodiments. It will be apparent to those skilled in the art that the elements, methods, systems, etc. of the technical solution of the embodiments of the present application can be changed, modified, altered, and evolved without departing from the principles, spirit, and scope of the embodiments and technical solutions of the present application as defined in the claims. These variations, changes, modifications, and evolution of embodiments are included in the equivalent embodiments of the present application, and these equivalent embodiments are included within the scope of the present application as defined by the claims. Although embodiments of the present application may be embodied in many different forms, some embodiments of the present invention are described in detail herein. In addition, embodiments of the present application include any possible combination of some or all of the various embodiments described herein and are also included within the scope of the present application as defined by the claims. All patents, patent applications and other cited materials mentioned in the present application or anywhere in any of the cited patents, cited patent applications or other cited materials are hereby incorporated by reference in their entirety.

The above disclosure is intended to be illustrative rather than exhaustive. Many variations and alternatives will be suggested to those skilled in the Art. All these alternatives and variations are intended to be included within the scope of the present claims, wherein the term "include" means "include, but not limited to".

The description of alternative embodiments of the present invention has been completed herein. Those skilled in the art will recognize other equivalent transformations of the embodiments described herein, which are also encompassed by the claims appended hereto.

INDUSTRIAL APPLICABILITY

The 3D bioprinting apparatus provided by the embodiments of the present invention includes a detachable 3D bioprinting pen device which can be operated in a hand-held manner to realize printing and repairing of damaged tissues or organs with simple operation and high flexibility. The 3D bioprinting method provided by the embodiments of the present invention does not need a fixed printing platform and can realize real-time and direct printing and repairing of tissues or organs.

What we claim is:

1. A 3D bioprinting apparatus comprising:
a printer frame (14), and
a 3D bioprinting pen device (4) arranged on the printer frame (14) and including a detachable printing pen (1) for 3D printing;
wherein the 3D bioprinting pen device (4) further comprises a pen body housing (7) and a connecting piece (10), and wherein the printing pen (1) is arranged inside the pen body housing (7) on which the connecting piece (10) is sleeved, and the pen body housing (7) is connected to the printer frame (14) by the connecting piece (10), wherein the detachable printing pen (1) is usable for 3D printing when detached.

2. The 3D bioprinting apparatus according to claim 1, wherein the 3D bioprinting pen device (4) further comprises a nozzle sleeve (9) which is sleeved outside the pen body housing (7), a rotatable L-shaped fixing latch (12) with a stop arm (12a) is provided over the top of the nozzle sleeve (9), and wherein the stop arm (12a) is configured to block the printing pen (1) when the stop arm (12a) is turned to the position on the top of the printing pen (1), and the printing pen (1) can be detached when the stop arm (12a) keeps away from the top of the printing pen (1).

3. The 3D bioprinting apparatus according to claim 1, wherein through holes (13) are provided on a side of the pen body housing (7), and a connecting piece through hole is provided in the connecting piece (10), and wherein a bolt passing through the connecting piece through hole and the through hole (13) of the pen body housing (7) fixes the pen body housing (7) to the connecting piece (10), thereby adjusting the height of the 3D bioprinting pen device (4).

4. The 3D bioprinting apparatus according to claim 1, wherein the bottom of the printing pen (1) comprises a print head (6).

5. The 3D bioprinting apparatus according to claim 1, wherein the printing pen (1) is provided with a lighting apparatus.

6. The 3D bioprinting apparatus according to claim 4, wherein the print head (6) is a conical fixed type print head (8) the end portion of which is provided with a fixed type UV point light source (5a).

7. The 3D bioprinting apparatus according to claim 4, wherein the print head (6) is a detachable rod-shaped hand-held print head (11), and a detachable UV point light source (5b) is sleeved on the middle of the hand-held print head.

8. The 3D bioprinting apparatus according to claim 5, wherein the printing pen (1) is provided with a lighting apparatus switch, optionally a UV point light source switch (15a).

9. The 3D bioprinting apparatus according to claim 1, wherein the printing pen (1) is provided with an air pump switch (15b).

10. The 3D bioprinting apparatus according to claim 5, wherein a lighting apparatus wiring channel is provided in the interior of the printing pen (1), optionally a UV point light source wiring channel.

11. A three-dimensional bioprinting method, using the three-dimensional bioprinting apparatus according to claim 1, comprising the steps of:
   establishing a 3D solid model to be printed, slicing it into layers, acquiring data information of each layer, and inputting the data information of each layer into a motion control system;
   preparing required polymer material and/or biomaterial, and placing the polymer material and/or biomaterial in a printing pen;
   controlling the printing pen by means of the motion control system to jet print the polymer material and/or biomaterial so that the polymer material and/or biomaterial directly act on and bond to a solid structure to be associated with the three-dimensional solid model, and optionally detaching the printing pen and carrying out a hand-held control operation to jet print the polymer material and/or biomaterial; and
   after one layer is printed, the printing pen being lifted by the height of one layer, and performing the jet printing step again to additively perform the printing layer by layer until the 3D solid model to be printed is directly printed on the solid structure.

12. The three-dimensional bioprinting method according to claim 11, wherein the polymer material and/or biomaterial is selected from one or more of the group consisting of a polymer material and/or biomaterial containing cells, a polymer material and/or biomaterial containing photoactive materials, and a polymer material and/or biomaterial containing non-photoactive materials.

13. The three-dimensional bioprinting method according to claim 12, wherein when the polymer material and/or biomaterial contains photoactive material, during the molding process of the polymer material and/or biomaterial, light emitted from point light source is irradiated on the polymer material and/or biomaterial ejected from the print head for curing the polymer material and/or biomaterial, or when the polymer material and/or biomaterial contains non-photoactive material, during the molding process of the polymer material and/or biomaterial, the polymer material and/or biomaterial is ejected onto the base solution in the molding area by a printing pen, and the solid structure is formed by chemical crosslinking.

14. The three-dimensional bioprinting method according to claim 11, wherein the solid structure may be a tissue or an organ to be repaired, and optionally bone tissue, cartilage, liver, kidney, skin, muscle, or blood vessel to be repaired.

15. The 3D bioprinting apparatus according to claim 2, wherein through holes (13) are provided on a side of the pen body housing (7), and a connecting piece through hole is provided in the connecting piece (10), and wherein a bolt passing through the connecting piece through hole and the through hole (13) of the pen body housing (7) fixes the pen body housing (7) to the connecting piece (10), thereby adjusting the height of the 3D bioprinting pen device (4).

16. The 3D bioprinting apparatus according to claim 1, wherein the bottom of the printing pen (1) comprises a print head (6).

17. The 3D bioprinting apparatus according to claim 1, wherein the printing pen (1) is provided with a lighting apparatus.

18. The 3D bioprinting apparatus according to claim 16, wherein the print head (6) is a conical fixed type print head (8) the end portion of which is provided with a fixed type UV point light source (5a).

19. The 3D bioprinting apparatus according to claim 16, wherein the print head (6) is a detachable rod-shaped hand-held print head (11), and a detachable UV point light source (5b) is sleeved on the middle of the hand-held print head.

* * * * *